US011141088B2

(12) United States Patent
Liu et al.

(10) Patent No.: US 11,141,088 B2
(45) Date of Patent: Oct. 12, 2021

(54) ELECTRONIC DEVICE FOR RECOGNITION OF MENTAL BEHAVIORAL ATTRIBUTES BASED ON DEEP NEURAL NETWORKS

(71) Applicant: SONY CORPORATION, Tokyo (JP)

(72) Inventors: Ming-Chang Liu, San Jose, CA (US); Ahmad Khodayari-Rostamabad, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 102 days.

(21) Appl. No.: 16/155,180

(22) Filed: Oct. 9, 2018

(65) Prior Publication Data
US 2020/0107766 A1    Apr. 9, 2020

(51) Int. Cl.
*A61B 5/16* (2006.01)
*A61B 5/00* (2006.01)
(Continued)

(52) U.S. Cl.
CPC .............. *A61B 5/165* (2013.01); *A61B 5/316* (2021.01); *A61B 5/369* (2021.01); *A61B 5/6814* (2013.01);
(Continued)

(58) Field of Classification Search
CPC ... A61B 5/6803; A61B 5/0478; A61B 5/6833; A61B 5/04012; A61B 5/04845;
(Continued)

(56) References Cited

U.S. PATENT DOCUMENTS

| 6,609,024 B1 | 8/2003 | Ryu et al. |
| 9,824,287 B2 * | 11/2017 | Wang ..................... A61B 5/352 |

(Continued)

FOREIGN PATENT DOCUMENTS

| CN | 102715902 A | 10/2012 |
| EP | 3576626 A1 | 12/2019 |
| WO | 2018/141061 A1 | 8/2018 |

OTHER PUBLICATIONS

Wilaiprasitporn, et al., "Affective EEG-Based Person Identification Using the Deep Learning Approach", Transactions on Cognitive and Developmental Systems, IEEE, vol. 14, No. 8, Aug. 2015, 10 pages.
(Continued)

*Primary Examiner* — Niketa I Patel
*Assistant Examiner* — Naveed R. Kolia
(74) *Attorney, Agent, or Firm* — Chip Law Group

(57) ABSTRACT

An electronic device that handles recognition of mental behavioral, affect, emotional, mental states, mental health, or mood-based attributes based on deep neural networks (DNNs), stores a set of EEG signals and a set of bio-signals associated with a subject. The electronic device trains a plurality of first recognition models on a training set of EEG signals and a training set of bio-signals associated with different training subjects. The electronic device trains a second recognition model on a feature vector from output layers of the plurality of first recognition models. The electronic device estimates a plurality of dependency or relationship data by application of the trained plurality of first recognition models on the set of EEG signals and bio-signals. The electronic device identifies a mental behavioral attribute of the subject by application of the trained second recognition model on the plurality of signals and their relationship data.

20 Claims, 6 Drawing Sheets

(51) Int. Cl.
*G06F 3/01* (2006.01)
*G06K 9/00* (2006.01)
*G06K 9/62* (2006.01)
*G06N 3/04* (2006.01)
*A61B 5/316* (2021.01)
*A61B 5/369* (2021.01)
*A61B 5/0205* (2006.01)

(52) U.S. Cl.
CPC ............ *A61B 5/7267* (2013.01); *G06F 3/015* (2013.01); *G06K 9/00892* (2013.01); *G06K 9/6227* (2013.01); *G06K 9/6254* (2013.01); *G06N 3/0454* (2013.01); *A61B 5/0205* (2013.01)

(58) Field of Classification Search
CPC ............... A61B 5/14542; G06N 20/00; G06K 9/00523; G06K 9/6293; G16H 50/20
See application file for complete search history.

(56) References Cited

U.S. PATENT DOCUMENTS

| | | | | |
|---|---|---|---|---|
| 2013/0116520 | A1* | 5/2013 | Roham | A61B 5/6833 600/324 |
| 2013/0178731 | A1* | 7/2013 | Bosl | A61B 5/369 600/409 |
| 2015/0297109 | A1* | 10/2015 | Garten | A61B 5/375 600/544 |
| 2016/0015289 | A1 | 1/2016 | Simon et al. | |
| 2017/0076740 | A1 | 3/2017 | Feast et al. | |
| 2017/0238868 | A1* | 8/2017 | Kenyon | A61B 5/4809 |
| 2017/0245778 | A1* | 8/2017 | Liu | A61B 5/6803 |
| 2019/0107888 | A1* | 4/2019 | Sereshkeh | A61B 5/378 |
| 2019/0192083 | A1* | 6/2019 | Laszlo | A61B 5/369 |
| 2020/0038671 | A1* | 2/2020 | Schulhauser | A61N 1/0484 |

OTHER PUBLICATIONS

Park, et al., "Solving the Memory-Based Memoryless Trade-off Problem for EEG Signal Classification", International Conference on Systems, Man, and Cybernetics (SMC), IEEE, Jan. 17, 2019, pp. 505-510.

Pant, et al., "Twin Neural Networks for Efficient EEG Signal Classification", International Joint Conference on Neural Networks (IJCNN), IEEE, Oct. 15, 2018, 8 pages.

Miranda-Correa, et al., "A Multi-Task Cascaded Network for Prediction of Affect, Personality, Mood and Social Context Using EEG Signals", 13th IEEE International Conference on Automatic Face & Gesture Recognition (FG 2018), Jun. 7, 2018, pp. 373-380.

International Search Report and Written Opinion of PCT Application No. PCT/IB2019/057167, dated Nov. 27, 2019, 15 pages of ISRWO.

* cited by examiner

ELECTRONIC DEVICE FOR RECOGNITION OF MENTAL BEHAVIORAL ATTRIBUTES BASED ON DEEP NEURAL NETWORKS

CROSS-REFERENCE TO RELATED APPLICATIONS/INCORPORATION BY REFERENCE

None.

FIELD

Various embodiments of the disclosure relate to deep learning technologies on neurophysiological activities of a human brain. More specifically, various embodiments of the disclosure relate to an electronic device for recognition of mental behavioral, affect or mental state attributes based on deep neural networks (DNNs).

BACKGROUND

Recent advancements in the field of biomedical signal processing have led to development of various methods and techniques for detection and further identification of different mental states, health conditions, and emotions experienced by users based on signal analysis of different bio-signals, e.g. brain waves through electroencephalogram (EEG) signals. Examples of the different mental states may include a stressed state, a relaxed state, a happy state, and the like. In conventional solutions, a conventional device may be configured to detect and identify different mental states, health conditions, and emotions based on implementation of a supervised machine learning platform that learn from bio-signals. In such an implementation, a conventional device may require input of hand crafted features to train a machine learning model and avoid a bias in the identification caused by lateralization of brain functions, which may be due to gender or handedness of individual users. Also, such models are capable of identifying simple features from a limited set of inputs, which further makes them unsuitable to identify complex features, relationships, or dependency among different functions in different regions of the brain.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic device for recognition of mental behavioral attributes based on deep neural networks (DNNs), and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
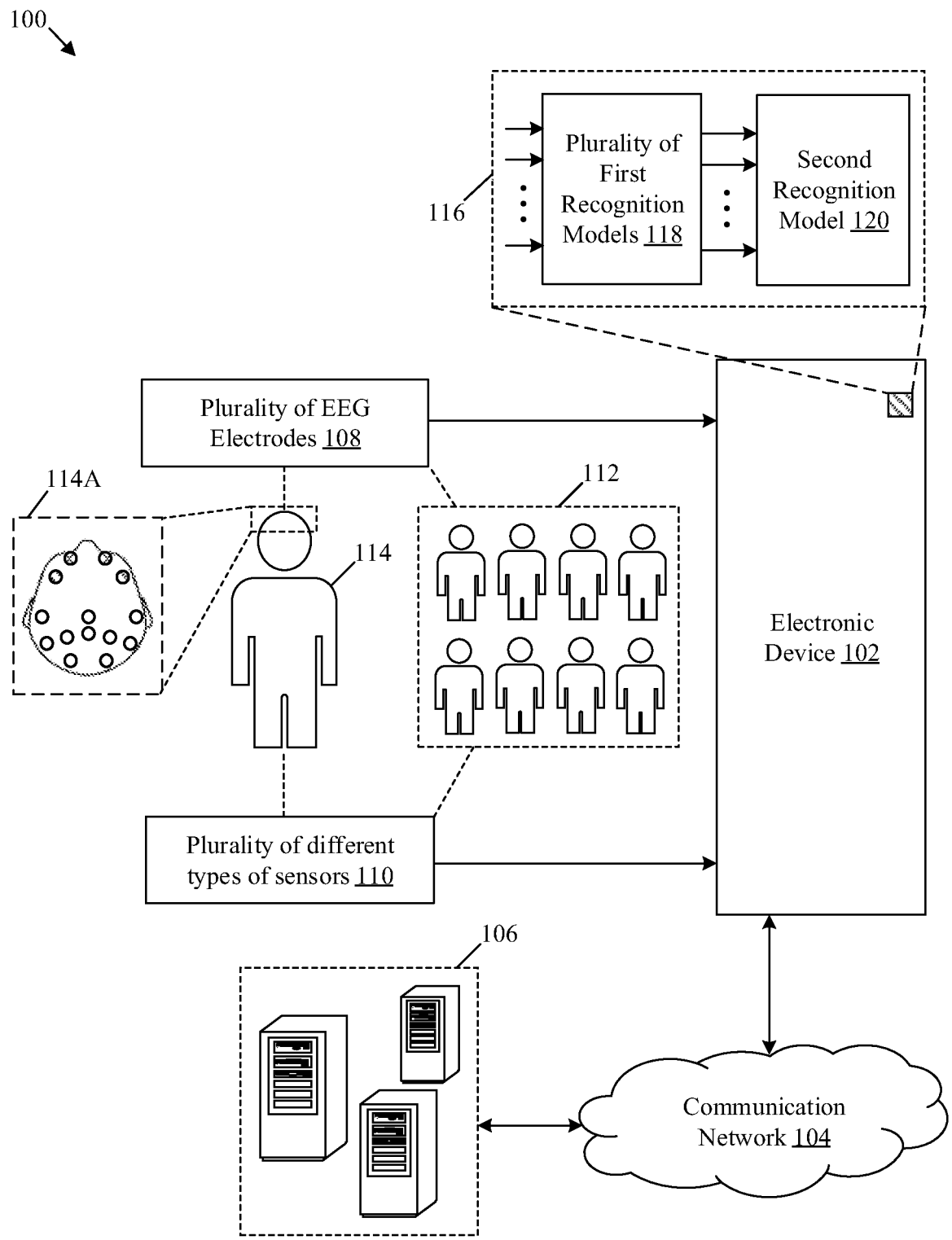
FIG. 1 is a block diagram that illustrates an exemplary environment that assists in recognition of mental behavioral attributes of a subject based on deep neural networks (DNNs), in accordance with an embodiment of the disclosure.

Various embodiments of the present disclosure may be found in a method and an electronic device that handles recognition of mental behavioral attributes or mental state attributes based on deep neural networks (DNNs). The present disclosure provides a robust solution to identify different mental behavioral attributes of a subject based on recognition and track of emotions, affects, mental states, or mental health conditions from different types of bio-signals (e.g., electroencephalogram (EEG) signals, photoplethysmogram (PPG) signals), wearable, and/or neurophysiological sensors. The electronic device utilizes a multi-level DNN model that trains on different simple and complex features of bio-signals from different training subjects. The training of the multi-level DNN model may ensure that an output of the trained multi-level recognition model may be invariant to different factors, such as an effect of lateralization of affect states, a gender, and a left-handedness, or a right-handedness of the subject. The multi-level DNN model may be utilized to identify simple and complex relationships, dependency, or a functional connectivity among different regions of the brain and other body parts that may indicate different mental behavioral attributes of a subject. The signals from each relevant group of sensors may be processed first by a first recognition model, and then results from the lower-level recognition model may be optimally combined to utilize the relationships and dependency between sensors and regions of the brain. All recognition models that extract discriminative and regional information, combine, and utilize data from various regions of the brain and body are built and learned from previously collected data.

In accordance with an embodiment, the disclosed method and the electronic device effectively and accurately recognizes mental health, wellness, mental states, emotions, mood or affective states based on lateral and hemispherical brain function when processing emotions and affective states, such as experiencing positive versus negative valence, positive versus negative emotions, highly concentrated or engaged versus neutral or dismissive conditions, or high arousal versus relaxing conditions. The disclosed electronic device employs relatively higher association of each brain hemisphere or region with certain kinds of mental or affective states or conditions. Thus, there is a significant improvement in handling of variability in mental states or affect processing as well as higher recognition accuracy, by effectively and automatically utilizing the differences in brain function and lateralization of affect processing in left-handed, right-handed, female, and male subjects. Further, the disclosed electronic device acts as a mental behavioral attributes monitor, mental wellness or affective intelligence processor that generates diagnostic, prognosis and prediction reports as they change over time. The disclosed electronic device also tracks changes in affective states, and provides feedback and advice in various forms, for example, recommendation of activities or practices to improve well-being, productivity, increase concentration or engagement, increase arousal, enhance positive emotions or valence or affects, to achieve a better mental health and wellness, an improved quality of life, productivity, or an improved performance.

FIG. 1 is a block diagram that illustrates an exemplary environment that assists in recognition of mental behavioral attributes of a subject based on a multi-level deep neural networks (DNNs), in accordance with an embodiment of the disclosure. With reference to FIG. 1, there is shown a network environment 100 that includes an electronic device 102, a communication network 104, and a data server 106. The electronic device 102 may be communicatively coupled to a plurality of different types of sensors 110 and a plurality of electroencephalogram (EEG) electrodes 108.

The electronic device 102 may comprise suitable logic, circuitry, interfaces, and/or code that may be configured to identify different mental behavioral attributes (e.g., affect states, emotion states, moods, mental states, mental conditions, etc.) of a subject 114 (i.e. a user of the electronic device 102) at different points in time. The electronic device 102 may be configured to operate in two different stages, i.e. a training stage and a deployment stage. In the training stage, the electronic device 102 may be configured to generate, build and train a multi-level recognition model 116 (based on DNNs) on different types of signals, such as EEG signals and bio-signals, from a set of training subjects 112. In the deployment stage, the trained multi-level recognition model 116 may be utilized by the electronic device 102 to generate different types of information or mental attributes particular to the subject 114, for example, mental health conditions, current mental state, current emotional state, current affective states, and the like. Examples of the implementation of the electronic device 102 may include, but are not limited to, an emotion-aware and emotionally responsive entertainment system, a gaming headset, an interactive wearable (such as a smart-watch, a smart-band, a smart necklace, a smart ear bud, smart clothes, or headphones), a gaming console, a non-wearable device, a virtual/augmented/mixed reality (VR/AR/MR) device, a mainframe computer, a handheld device, a cellular/mobile phone, a smart television, and various forms of mental, psychological and physical health, wellness, and fitness measurement and monitoring devices.

The communication network 104 may include a medium through which the electronic device 102 may communicate with the server 106. Examples of the communication network 104 may include, but are not limited to, the Internet, a cloud network, a Long Term Evolution (LTE) network, a Wireless Local Area Network (WLAN), a Local Area Network (LAN), a telephone line (POTS), and/or a Metropolitan Area Network (MAN). Various devices in the network environment 100 may be configured to connect to the communication network 104, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), ZigBee, EDGE, IEEE 802.11, light fidelity (Li-Fi), 802.16, IEEE 802.11s, IEEE 802.11g, multi-hop communication protocols, wireless access point (AP) protocols, device to device communication protocols, cellular communication protocols, or Bluetooth (BT) communication protocols, or a combination thereof.

The server 106 may comprise suitable circuitry, interfaces, and/or code that may be configured to operate as a centralized computing server that may handle a portion or all the functionalities of the electronic device 102. For example, the server 106 may be configured to build, train, and utilize a multi-level recognition model 116 to output different types of information related to mental behavioral attributes of different subjects, e.g. the subject 114. In such a case, the server 106 may be configured to output such types of information, based on EEG signals and bio-signals from different training subjects. The server 106 may be configured to communicate with the electronic device 102, via the communication network 104. Examples of the server 106 may include, but are not limited to, an application server, a cloud server, a web server, a database server, a file server, a gaming server, a mainframe server, or a combination thereof.

The plurality of EEG electrodes 108 may be specialized non-invasive or invasive electrodes that may be placed around different regions of forehead, face or the scalp that surrounds the cerebral cortex of the brain of the set of training subjects 112 and the subject 114 (as shown in a view 114A). The plurality of EEG electrodes 108 may act as a receiver and carrier of the set of EEG signals from the set of training subjects 112 and the subject 114. Examples of the plurality of EEG electrodes 108 may include, but are not limited to, EEG electrode caps, EEG electrode bands, reusable disk-based electrodes, adhesive gel electrodes, and sub-dermal needle-based electrodes. In one example, the plurality of EEG electrodes 108 may be implemented inside a virtual reality (VR) headset or glass, an augmented reality (AR) headset or glass, a mixed reality headset or glass, a gaming headset, a gaming glass, or a mentally or emotionally interactive headset or cap.

The plurality of different types of sensors 110 may comprise suitable circuitry, interfaces, and/or code that may be configured to capture a set of different types of bio-signals from the subject 114 and the set of training subjects 112. Examples of the set of different types of bio-signals may include, but are not limited to, an ECG or EKG signal, sweat analysis signal, a galvanic skin response (GSR) signal, respiration or breathing signal, a photoplethysmogram (PPG) signal, a mechanomyogram (MMG) signal, near-infrared spectroscopy signal, and a magneto encephalogram (MEG) signal. The plurality of different types of sensors 110 may include a set of neurophysiological sensors, a set of bio-sensors, or a set of wearable sensors. Examples of the plurality of different types of sensors 110 may include, but are not limited to, an electrochemical bio-sensor, an amperometric bio-sensor, a blood glucose bio-sensor, a potentiometric bio-sensor, a piezoelectric bio-sensor, a sweat analysis bio-sensor, and a thermometric bio-sensor. Examples of implementation of the plurality of different types of sensors 110 may include, but are not limited to, a smart watch, a smart band, an ECG sensor, a magnetic resonance imaging (MRI) scanner, a PPG sensor, a micro-electro-mechanical system (MEMS) sensor, and a positron emission tomography (PET) scanner.

In operation, the electronic device 102 may be configured to operate in one or more operational stages, which may include at least a training stage and a deployment stage. The training stage may be an online training stage or an offline training stage, based on a requirement or suitable usage of the electronic device 102. In the online stage, the electronic device 102 may be configured to train a multi-level recognition model 116 (based on DNNs) in a single step at a time based on availability of training data. The training data may include a training set of EEG signals and a training set of different types of bio-signals from the set of training subjects 112. In such case, the training data may be continuously fed to the multi-level recognition model 116 from the server 106 while different learning parameters (e.g., weight parameters) of the multi-level recognition model 116 still adapts to the training data. Similarly, in the offline stage, the electronic device 102 may be configured to train the multi-level recognition model 116 with a batch of training data at once. The learning parameters may be adjusted based on the batch of the training data and thereafter, the electronic device 102 may be configured to utilize the trained multi-level recognition model 116 at the deployment stage to yield different results for the subject 114.

In the training stage, the electronic device 102 may be configured to store a set of EEG signals and a set of bio-signals associated with each training subject of the set of training subjects 112. In accordance with an embodiment, training data that may include the set of EEG signals and the set of different types of bio-signals may be retrieved from the server 106 as updates at different points in time. In accordance with another embodiment, the electronic device 102 may be configured to capture the set of EEG signals and the set of different types of bio-signals in real time from the set of training subjects 112 in order to train multi-level recognition model 116 integrated in the electronic device 102. In certain embodiments, the set of EEG signals and the set of different types of bio-signals are captured as analog signals, which are sampled (for example, a signal frame sampled at 200 Hz for 20 seconds) and digitized for storage in the electronic device 102. The set of EEG signals may include a first set of EEG signals from a left portion and a second set of EEG signals from a right portion of the cerebral cortex of the brain of each training subject of the set of training subjects 112. The first set of EEG signals and the second set of EEG signals may be captured through the plurality of EEG electrodes 108, which are placed on scalp or forehead of each training subject of the set of training subjects 112.

The set of different types of bio-signals may be captured by the plurality of different types of sensors 110 associated with each subject of the set of training subjects 112. Examples of the set of different types of bio-signals may include, but are not limited to, an electrocardiogram signal, a sweat analysis signal, an electromyogram signal, a galvanic skin response signal, and a magneto encephalogram signal. The plurality of different types of sensors 110 may be placed at different body parts, at left and or right sides, (such as wrist, fingers, thigh, hip, neck, face, or head) of each of the plurality of training subject. The set of different types of bio-signals captured from the set of training subjects 112 at a particular time interval, may indicate a mental state, a physiological state, or a neurophysiological state of each of the set of training subjects 112.

In one example, in order to capture training data associated with emotional states, affect states, left-handedness, or right-handedness, the electronic device 102 may be configured to capture the first set of EEG signals with a first set of EEG electrodes 110A of the plurality of EEG electrodes 108. The first set of EEG signals may include a left pre-frontal cortex EEG signal captured from a left portion of a pre-frontal cortex of each training subject of the set of training subjects 112. The first set of EEG signals may further include a left frontal cortex EEG signal captured from left portion of the frontal cortex of each training subject of the set of training subjects 112. In another example, the electronic device 102 may be configured to capture a second set of EEG signals with a second set of EEG electrodes 110B of the plurality of EEG electrodes 108. The second set of EEG signals may include a right pre-frontal EEG cortex signal captured from a right portion of a pre-frontal cortex of each training subject of the set of training subjects 112. The second set of EEG signals may further include a right frontal cortex EEG signal captured from right portion of the frontal cortex of each training subject of the set of training subjects 112. The first set of EEG signals and the second set of EEG signals may indicate brain function of each of the plurality of training subjects at a particular time interval, within which the first set of EEG signals and the second set of EEG signals may be captured from the set of training subjects 112.

The electronic device 102 may be further configured to train a plurality of first recognition models 118 on a training set of EEG signals and a training set of different types of bio-signals associated with the set of training subjects 112. The plurality of first recognition models 118 may correspond to a first plurality of deep neural networks (DNNs) arranged in a parallel architecture. In the parallel architecture, all the DNNs may be trained as per a parallel processing scheme by the electronic device 102 and a single DNN may receive one or more signals as an input from the training set of EEG signals and the training set of different types of bio-signals. Each of the plurality of first recognition models 118 may be implemented based on a same or a different DNN of the first plurality of DNNs as part of one of: a supervised learning model, an unsupervised learning model, or a reinforcement learning model. The first plurality of DNNs may correspond to one or more recognition layers of a multi-level DNN for extraction of different features (e.g. in terms of a feature map and/or a feature vector) for recognition of different mental behavioral attributes of the subject 114. Examples of the first plurality of DNNs may include, but are not limited to, a recurrent neural network (RNN), a convolutional neural network (CNN), a Long Short Term Memory (LSTM)-based RNN, a gated recurrent unit (GRU)-based RNN, a fully connected neural network, a Connectionist Temporal Classification (CTC)-based RNN, a deep Bayesian neural network, a Generative Adversarial Network (GAN), or a combination of such networks.

In accordance with an embodiment, each recognition model of the plurality of first recognition models 118 may be separately trained on a specific type of signal from the training set of EEG signals and the training set of different types of bio-signals. In accordance with an embodiment, each of the plurality of first recognition models 118 may be trained separately, based on different brain functions in a different hemisphere of the brain of each of the set of training subjects 112. Alternatively stated, each of the plurality of first recognition models 118 may be trained individually, based on lateral or hemispherical brain function of each subject of the set of training subjects 112.

The first set of EEG signals may indicate different active brain functions in a first region or a first hemisphere (such as a left hemisphere) of the brain of each of the plurality of training subjects 112. The second set of EEG signals may indicate different brain functions in a second region or a second hemisphere (such as a right hemisphere) of the brain of each of the set of training subjects 112. The electronic device 102 may be further configured to train a second recognition model 120 on a feature vector outputted from output layers of the plurality of first recognition models 118. The second recognition model 120 may correspond to a second plurality of DNNs. The second plurality of DNNs may correspond to one or more recognition layers of a multi-level DNN for recognition of different mental behavioral attributes of the subject 114, based on features extracted from the first plurality of DNNs. Examples of the second plurality of DNNs may include, but are not limited to, a RNN, a CNN, an LSTM-based RNN, a CTC-based RNN, and a GAN.

In accordance with an embodiment, the electronic device 102 may be configured to adjust a plurality of weight parameters associated with the plurality of first recognition models and the second recognition model 120. The plurality of weight parameters may be adjusted by iterative application of an optimization scheme on the plurality of weight parameters. The adjustment of the plurality of weight parameters may correspond to a training of the plurality of first recognition models 118 and the second recognition model 120. Examples of the optimization scheme may include, but are not limited to, a gradient descent, a stochastic gradient descent (SGD), and a mini-batch gradient descent, Adagrad, Adadelta, and Adaptive Moment Estimation (ADAM).

The training of the plurality of first recognition models 118 and the second recognition model 120 may be adapted to ensure that the trained multi-level recognition model 116 are robust enough to detect different mental behavioral attributes from different brain functions. The brain functions may be implicitly indicated by signal patterns (or fingerprints) of the set of EEG signals and the set of different types of bio-signals. More specifically, the training of the multi-level recognition model 116 may ensure that an output of the trained multi-level recognition model 116 may be invariant to different factors, such as an effect of lateralization of affect states, a gender, and a left-handedness, or a right-handedness of the subject 114.

In the deployment stage, the electronic device 102 may be associated with the subject 114, who may be a sole user (or part of a group of users) of the electronic device 102. For example, in the deployment stage, the electronic device 102 may be a VR headset (or part of a VR headset) for a VR-based gaming console that may be worn by the subject 114 while playing a VR game. In such a case, the electronic device 102 include an EEG cap/headband inside the VR headset that may record and utilize different bio-signals to generate different results, such as emotional states at different point in time in the gameplay.

The electronic device 102 may be configured to estimate a plurality of relationship or dependency data by application of the trained plurality of first recognition models 118 on the set of EEG signals and the set of different types of bio-signals associated with the subject 114. The plurality of relationship data may indicate a functional connectivity or a dependency between different regions of a brain or body (as shown from the view 114A) of the subject 114. As an example, a relationship data may indicate that a region in the left frontal lobe of the brain responsible for emotion or affect processing may have a functional connectivity with a region in the right frontal lobe at the time a left-hand of the subject 114 is engaged in the gameplay. The plurality of relationship data may indicate granular attributes from different regions of the brain and other parts of the body, which may be suitable for a higher-level deep neural network to detect or estimate a mental behavioral attribute at specific time intervals. As another example, the plurality of dependency or relationship data may indicate a rate at which one of the first set of EEG signals may vary with respect to variation in one of the second set of EEG signals, or the first set of input bio-signals.

In accordance with an embodiment, instead of having an offline training for the multi-level recognition model 116, the electronic device 102 may be configured to store pre-trained multi-level recognition model 116 for use by a user (e.g., a new subject, a new user, or the subject 114) of the electronic device 102. In such a case, the pre-trained models may still be updated at different points in time to recognize new (or unrecognized) mental behavioral attributes of the user (or the subject 114). The electronic device 102 may be configured to input the set of EEG signals and the set of different types of bio-signals associated with the subject 114 to a plurality of first recognition models 118 pre-trained on a training set of EEG signals and a training set of different types of bio-signals. Thereafter, the electronic device 102 may be configured to estimate a plurality of relationship data, which may indicate a functional connectivity or a dependency between different regions of a brain of the subject 114, by application of the plurality of first recognition models 118 on the set of EEG signals and the set of different types of bio-signals associated with the user (i.e., the new user or the subject 114).

The electronic device 102 may be further configured to identify a mental behavioral attribute of the subject 114 from a set of mental behavioral attributes, by application of the trained second recognition model 120 on the estimated plurality of relationship data. The identification of the mental behavioral attribute may be unsupervised based on automatic feature extraction and selection on the basis of regularly adjusted weight parameters at each layer of the DNNs in the plurality of first recognition models 118 and the second recognition model 120. The set of mental behavioral attributes may include, but are not limited to, a set of affect states, a set of emotional states, a set of mental health conditions, a set of mental states, and a set of mood-based attributes. In some embodiments, an output layer of the trained second recognition model 120 may further act as a classifier to identify the mental behavioral attribute which has a maximum likelihood among the set of mental behavioral attributes. The classifier may be one of: a random forest based classifier, a support vector machine (SVM) based classifier, a logistic regression-based classifier, a linear regression-based classifier, a Softmax classifier, a Bayesian estimation network classifier, a deep neural network classifier and the like.

As an example, the mental behavioral attribute may indicate an affective state, an experienced or expressed/unexpressed emotion, an identifier for a mental health condition, or a general wellness of the subject 114 (or the user) associated with the electronic device 102. The mental behavioral attribute may distinguish between positive versus negative valence, positive versus negative emotions, and high arousal versus relaxing conditions for the subject 114.

In accordance with an embodiment, the electronic device 102 may be configured to track changes in different mental behavioral attributes of the subject 114 over a time period, for example, in a period associated with a gameplay on a VR headset. Thereafter, the electronic device 102 may be configured to generate a diagnostic report, a prognosis report and a prediction report for the subject 114 based on the tracked changes in different mental behavioral attributes. The generation of such reports may be part of a feedback scheme incorporated along with the multi-level recognition model 116. The diagnostic report, the prognosis report, and the prediction report may be generated further based on one or more user parameters associated with the subject 114. The electronic device 102 may be configured to store a plurality of user parameters associated with the subject 114. The plurality of user parameters may include an age, a gender, a handedness, an intelligence quotient (IQ), and a sexual orientation of the subject 114.

The diagnostic report may include information associated with the different mental behavioral attributes identified over a period of time. The prognosis report may include information possible recommendations over an impact of such attributes on the mental health of the subject 114 to a certain extent. The prediction report may include information associated with one or more courses of action, which may be undertaken by the subject 114 to alleviate a possible effect on mental health, wellness, or a general wellbeing of the subject 114. For example, the prediction report may include information associated with a recommended method to improve mental health, wellness, performance, and a quality of life of the subject 114.

Some of the exemplary scenarios have been described herein. In an exemplary scenario, the subject 114 may be engaged in playing a video game on a gaming console, for example, a VR gaming console. The VR gaming console (i.e., the electronic device 102) may be configured to set a difficulty level for the video game based on an identified mental state of the subject 114. For example, in cases where the identified mental state is a relaxed mental state, then the VR gaming console may be configured to increase the difficulty level of the video game. In cases where the identified mental state is a stressed mental state, then the VR gaming console may be configured to decrease the difficulty level of the video game.

In another exemplary scenario, the subject 114 may have ingested an anti-depressant or a painkiller as part of a daily medication. The electronic device 102 (e.g., a headband and a smart watch) may be configured to measure an efficacy value of the medication based on the identified mental state. For example, in cases where the identified mental state of the subject 114 is a depressed mental state or a painful mental state, then the electronic device 102 may be configured to identify the ingested anti-depressant or painkiller medication as ineffective for the subject 114. Otherwise, the electronic device 102 may be configured to identify the ingested anti-depressant or painkiller medication as effective for the subject 114.

In yet another scenario, the subject 114 may be driving a car. In such scenarios, the electronic device 102 may be configured to identify the mental state of the subject 114 to decide whether to alert the subject 114 or not. In cases where the identified first mental state of the subject 114 is a sleepy or semiconscious mental state, then the electronic device 102 may be configured to generate an alert for the subject 114.

Figure 2:
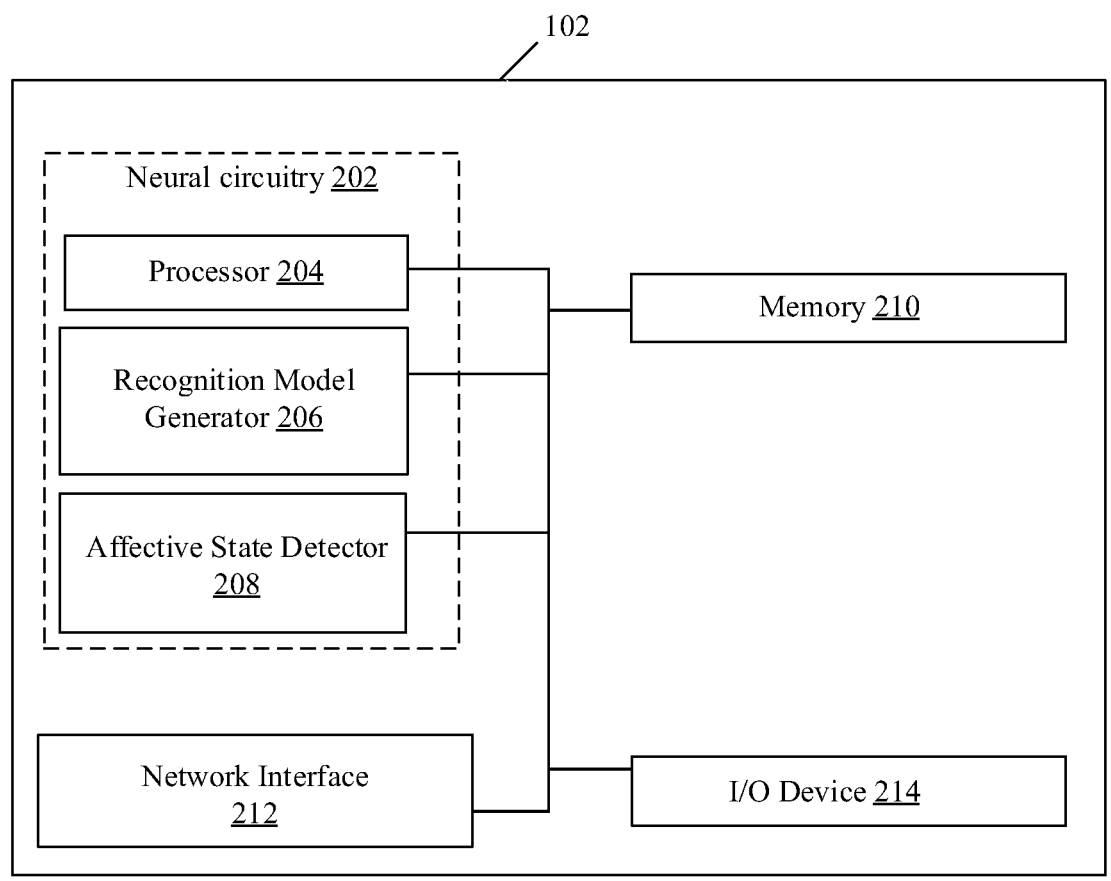
FIG. 2 is a block diagram that illustrates an exemplary an electronic device for recognition of mental behavioral attributes of a subject based on DNNs, in accordance with an embodiment of the disclosure.

FIG. 2 is a block diagram that illustrates an exemplary an electronic device for recognition of mental behavioral attributes of a subject based on DNNs, in accordance with an embodiment of the disclosure. FIG. 2 is explained in conjunction with elements from FIG. 1. With reference to FIG. 2, the electronic device 102 may include neural circuitry 202, which may include a processor 204, a recognition model generator 206, and an affective state detector 208. Although not shown, in some embodiments, the neural circuitry 202 may include different DNN-specific circuitries that may be implemented along with an artificial intelligence (AI) accelerator chip. The AI accelerator chip may be configured to accelerate a learning rate or an optimization rate of loss function (i.e. error function) for the multi-level recognition model 116. The electronic device 102 may further include a memory 210, a network interface 212, and an input/output (I/O device) 214.

The processor 204 may comprise suitable logic, circuitry, interfaces, and/or code that may be configured to execute a set of instructions stored in the memory 210. The processor 204 may be configured to process a set of EEG signals and a set of different types of bio-signals captured by the neural circuitry, using the plurality of EEG electrodes 108 and the plurality of different types of sensors 110. The processor 204 may be configured to estimate the plurality of relationship data between a first set of EEG signals, a second set of EEG signals, and the set of different types of bio-signals. Examples of the processor 204 may include an Application-Specific Integrated Circuit (ASIC) processor, a Complex Instruction Set Computing (CISC) processor, and/or other hardware processors.

The recognition model generator 206 may comprise suitable logic, circuitry, interfaces, and/or code that may be configured to generate and train the plurality of first recognition models 118 based on the set of EEG signals and the set of different types of bio-signals. Examples of implementations of the recognition model generator 206 may be an x86-based processor, a GPU, a RISC processor, an ASIC processor, a CISC processor, a microcontroller, a CPU, and/or other control circuits.

The affective state detector 208 may comprise suitable logic, circuitry, interfaces, and/or code that may be configured to identify different mental behavioral attributes of the subject 114 by application of the second recognition model 120 on different feature vectors extracted from plurality of first recognition models 118. Examples of implementations of the affective state detector 208 may be an x86-based processor, a GPU, a RISC processor, an ASIC processor, a CISC processor, a microcontroller, a CPU, and/or other control circuits.

The memory 210 may comprise suitable logic, circuitry, and/or interfaces that may be configured to store a set of instructions executable by the neural circuitry 202, such as the processor 204, the recognition model generator 206, and the affective state detector 208. The memory 210 may be configured to store a set of instructions or program code associated with the multi-level recognition model 116, a set of EEG signals, a set of different types of bio-signals, and a plurality of user parameters associated with the subject 114. In certain embodiments, the memory 210 may also store similar data for the set of training subjects 112. Examples of implementation of the memory 210 may include, but are not limited to, Random Access Memory (RAM), Read Only Memory (ROM), Hard Disk Drive (HDD), and/or a Secure Digital (SD) card.

The network interface 212 may comprise suitable logic, circuitry, interfaces, and/or code that may be configured to enable communication between the electronic device 102 and the server 106, via the communication network 104. The network interface 212 may implement known technologies to support wired or wireless communication with the communication network 104. The network interface 212 may include, but is not limited to, an antenna, a frequency modulation (FM) transceiver, a radio frequency (RF) transceiver, one or more amplifiers, a tuner, one or more oscillators, a digital signal processor, a coder-decoder (CODEC) chipset, a subscriber identity module (SIM) card, and/or a local buffer.

The network interface 212 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as Long Term Evolution (LTE), Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.120g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The I/O device 214 may comprise suitable logic, circuitry, interfaces, and/or code that may be configured to receive a plurality of inputs from the user. The I/O device 214 may comprise various input and output devices that may be configured to communicate with the electronic device 102 and the server 106. Examples of the input devices may include, but not limited to, a touch screen, a keyboard, a mouse, a joystick, a microphone, a gesture controller, and/or an image sensor. Examples of the output devices may include, but not limited to, a display screen (such as a Liquid Crystal Display (LCD) or a Light Emitting Diode (LED) display) and/or a speaker. The details of the operation of the electronic device 102 has been further described in detail, for example, in FIG. 3 and FIG. 4.

Figure 3:
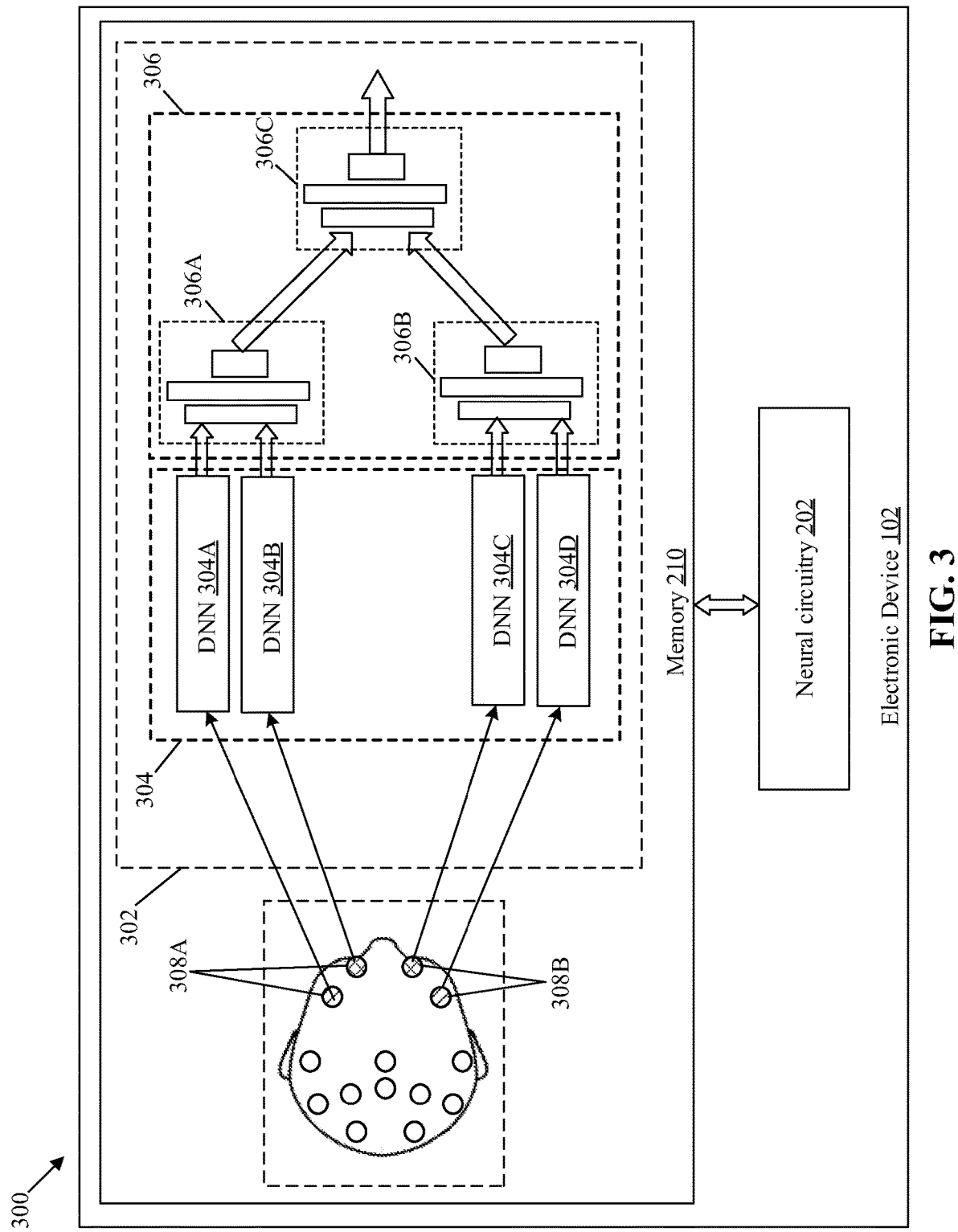
FIG. 3 illustrates a first exemplary scenario for implementation of the electronic device of FIG. 2 for recognition of mental behavioral attributes of a subject based on DNNs, in accordance with an embodiment of the disclosure.

FIG. 3 illustrates a first exemplary scenario for implementation of the electronic device of FIG. 2 for recognition of mental behavioral attributes of a subject 114 based on DNNs, in accordance with an embodiment of the disclosure. FIG. 3 is explained in conjunction with elements from FIGS. 1 and 2. With reference to FIG. 3, there is shown a first exemplary scenario 300 for implementation of the electronic device 102.

In the first exemplary scenario 300, there is shown a multi-level recognition model 302 stored in the memory 210. The multi-level recognition model 302 may be trained on a training set of EEG signals and a training set of different types of bio-signals. The training set of EEG signals may be obtained from different regions of the brain of different training subjects of the set of training subjects 112. In some embodiments, instead of individual training sets, the neural circuitry 202 may be configured to create different mini-batches of training sets for specific types of signal (e.g., EEG, PPG, etc.) from different regions of the brain and other body parts, respectively. Similarly, the set of different types of bio-signals associated with the set of training subjects 112 may be captured by the plurality of different types of sensors 110. The plurality of different types of sensors 110 may be placed on different body parts of each subject of the set of training subjects 112. Examples of the plurality of different types of sensors 110 may include, but are not limited to, a set of neurophysiological sensors, a set of biosensors, and a set of wearable sensors.

The multi-level recognition model 302 may include a plurality of first recognition models 304 and a second recognition model 306 that acts as the last stage for recognition of different mental behavioral attributes of the subject 114. The plurality of first recognition models 304 may be implemented as a first set of DNNs arranged in parallel to receive the set of EEG signals and the set of different types of bio-signals as training and test data. The plurality of first recognition models 304 may include a first DNN 304A, a second DNN 304B, a third DNN 304C, and a fourth DNN 304D. The first DNN 304A, the second DNN 304B, the third DNN 304C, and the fourth DNN 304D may correspond to an initial input-level of the multi-level recognition model 302. In accordance with an embodiment, the first DNN 304A may be trained based on an EEG signal received from a left frontal cortex region of the brain, via a first set of EEG electrodes 308A. The second DNN 304B may be trained based on an EEG signal received from a left pre-frontal cortex region of the brain, via the first set of EEG electrodes 308A. The third DNN 304C may be trained based on an EEG signal received from a right frontal cortex region of the brain, via a second set of EEG electrodes 308B. The fourth DNN 304D may be trained based on an EEG signal received from a right pre-frontal cortex region of the brain, via the second set of EEG electrodes 308B. In accordance with an embodiment, the first DNN 304A, the second DNN 304B, the third DNN 304C, and the fourth DNN 304D may be trained on a combination of the set of EEG signals and the set of different types of bio-signals. Although not shown, the first DNN 304A, the second DNN 304B, the third DNN 304C, and the fourth DNN 304D may have two or more inputs to at least receive, as input, an EEG signal, a type of bio-signal, or a combination thereof.

Each of the first DNN 304A, the second DNN 304B, the third DNN 304C, and the fourth DNN 304D may be trained separately by use of a specific type of signal from the training set of EEG signals and the training set of different types of bio-signals. For example, the first DNN 304A and the second DNN 304B may be trained on functional activities that occur in the left-hemisphere of the brain, for example, the left pre-frontal cortex. Similarly, the third DNN 304C and the fourth DNN 304D may be trained on right hemisphere of the brain, for example, the right frontal cortex. The EEG signal from the left pre-frontal cortex and the left frontal cortex may be associated with brain function in the left hemisphere of each subject of the set of training subjects 112 and the subject 114. The EEG signal from right pre-frontal cortex and the right frontal cortex signal may be associated with brain function in the right hemisphere of each subject of the set of training subjects 112 and the subject 114.

The neural circuitry 202 may be configured to train the second recognition model 306 for recognition of the plurality of mental behavioral attributes of the subject 114. The neural circuitry 202 may be configured to train the second recognition model 306 based on a feature vector outputted from output layers of the plurality of first recognition models. The feature vector may represent an estimate of a plurality of relationship or dependency data among different regions of the brain of each training subject of the set of training subjects 112. In some embodiments, the second recognition model 306 may be trained further based on the plurality of user parameters and/or a combination of the output feature vector of the trained plurality of first recognition models.

In certain scenarios, the set of mental behavioral attributes may include a first set of mental behavioral attributes and a second set of mental behavioral attributes. In one example, the first set of mental behavioral attributes may be positive mental behavioral attributes and the second set of mental states may be negative mental behavioral attributes. The positive mental behavioral attributes may correspond to positive emotional states (e.g., positive sentiments, affections), positive affect states, positive valences, a good mood, or factors that improve or indicate improvements in mental health conditions of the subject 114. For example, the positive mental behavioral attributes may include, but are not limited to, emotional states, such as a happy state, an excited state, a contented state, an elated state, an alert state, and a relaxed state, an intensity of emotions, and affect states based on pleasant behavior, pleasant facial expressions, heart rate patterns, or functional brain activities. Similarly, the negative mental behavioral attributes may correspond to negative emotional states (e.g., negative sentiments), negative affect states, negative valences, a bad mood, or factors that cause a decline or indicate a decline in mental health conditions of the subject 114. For example, the positive mental behavioral attributes may include, but are not limited to, emotional states, such as a sad state, a nervous state, a stressed state, an upset state, a depressed state, and a bored state, an intensity of emotions, and affect states based on unpleasant behavior, unpleasant facial expressions, heart rate patterns, or functional brain activities.

The neural circuitry 202 may be configured to compute an interconnectivity parameter and a dependency parameter between each of the first set of mental behavioral attributes and the first set of mental behavioral attributes. The second recognition model 306 may be further trained based on an interconnectivity parameter and a dependency parameter between a first set of mental behavioral attributes of the set of mental behavioral attributes and a second set of mental behavioral attributes of the set of mental behavioral attributes. The interconnectivity parameter may indicate a functional connectivity between different regions of the brain of the subject 114, while the brain stays functional for two or more mental behavioral attributes. For example, a portion of the EEG signal may indicate interconnectivity between a sad emotional state of the subject 114 and a movement of left hand placed on a gaming console. Such interconnectivity may be described by an interconnectivity parameter that may map activity in the left pre-frontal lobe for the sad emotion state to a particular region in the right frontal lobe for the left hand movement. Similarly, the dependency parameter may indicate how one mental behavioral attribute affects another mental behavioral attribute in a timeline of a plurality of mental behavioral attributes measured over a time period. For example, the dependency parameter may indicate a sequence of relationships among different emotions experienced by the subject 114 in a particular time period while the subject was engaged in a gameplay.

The second recognition model 306 (i.e. a higher-level recognition model than each of the plurality of first recognition models 304) may be trained by the neural circuitry 202, to optimally combine output feature vector(s) from the plurality of first recognition models 304. The neural circuitry 202 may be configured to utilize the trained second recognition model 306 to extract information associated with the interconnectivity and dependency among different mental behavioral attributes of the subject 114.

The second recognition model 306 may include a fifth DNN 306A, a sixth DNN 306B, and a seventh DNN 306C. The fifth DNN 306A, the sixth DNN 306B, and the seventh DNN 306C may correspond to one or more higher-level layers of the multi-level recognition model 302. The neural circuitry 202 may be configured to train the fifth DNN 306A, based on a first output of the first DNN 304A and a second output the second DNN 304B. The fifth DNN 306A may be trained to optimally combine the first output and the second output. The neural circuitry 202 may be further configured to train the sixth DNN 306B based on a third output of the third DNN 304C and a fourth output of the fourth DNN 304D. The neural circuitry 202 may be further configured to train the seventh DNN 306C based on a fifth output of the fifth DNN 306A and a sixth output of the sixth DNN 306B. The seventh DNN 306C may be trained to optimally combine the fifth output and the sixth output. An output layer of the second recognition model 306 may act as a classifier to identify the mental behavioral attribute which has a maximum likelihood among the set of mental behavioral attributes. The classifier may be one of a random forest based classifier, a support vector machine (SVM) based classifier, a logistic regression-based classifier, a linear regression-based classifier, a Softmax classifier, a Bayesian estimation network classifier, a deep neural network classifier.

The neural circuitry 202 may be further configured to evaluate and optimize the trained plurality of first recognition models 304 and the trained second recognition model 306 by using a randomly selected training, validation and test data subsets, or by application of one or more levels of k-fold cross-validation of the training set of EEG signals and the training set of bio-signals. In k-fold cross-validation, k represents a number of folds required for cross-validation of the trained plurality of first recognition models 304 and the trained second recognition model 306.

In the deployment stage, based on the trained plurality of first recognition models 304, the neural circuitry 202 may be configured to estimate a plurality of relationship data. The relationship data may indicate a functional connectivity or a dependency between different regions of a brain of the subject 114. The plurality of dependency or relationship data may be indicated by an output feature vector that may be generated after an application of the trained plurality of first recognition models 304 on the set of EEG signals and the set of different types of bio-signals associated with the subject 114. The interconnectivity or dependency of different EEG signals or bio-signals from the set of EEG signals or the set of different types of bio-signals with each other may indicate a dependency of different functional areas of the brain while the brain of the subject 114 undergoes a cognitive or neurophysiological activity. For example, a sad emotional state may be indicated by activity in the left hemisphere of the brain which may further show a dependency on an area of brain that processes physical pain. Thus, the physical pain and the sad emotional state may have a dependency as an output feature from the plurality of first recognition models 304. The plurality of dependency or relationship data may also indicate an association of each of the plurality of user parameters of each user, with the brain function of each hemisphere of the brain of the respective user.

In accordance with an embodiment, the neural circuitry 202 may be further configured to identify a mental behavioral attribute of the subject 114 from a set of mental behavioral attributes, by application of the trained second recognition model on the estimated plurality of dependency or relationship data. The set of mental behavioral attributes may include a set of affect states, a set of emotional states, a set of mental health conditions, a set of mental states, and a set of mood-based attributes. In some embodiments, a current mental behavioral attribute of the subject 114 may be identified based on analysis of intermediate layers or an output layer of the second recognition model 306.

A plurality of mental behavioral attributes of the subject 114 may be identified over a time period further based on the estimated plurality of dependency or relationship data. Alternatively stated, the plurality of mental behavioral attributes may be identified based on the association of a mental behavioral attribute with a corresponding brain function of each hemisphere of the brain of the respective subject 114. In accordance with an embodiment, the neural circuitry 202 may be further configured to receive the output feature vector of the trained plurality of first recognition models 304 and an output feature vector of the trained second recognition model 306. The mental behavioral attribute of the subject 114 may be identified based on the received output feature vector of the trained plurality of first recognition models and the trained second recognition model.

The neural circuitry 202 may be further configured to map, over a time period, a plurality of mental behavioral attributes of the subject 114 to a plurality of signal samples of the set of EEG signals and the set of different types of bio-signals associated with the subject 114. Examples of the plurality of mental behavioral attributes may include, but are not limited to, a happy state, a sad state, an attentive state, a painful state, a stressed state, and a relaxed state. The neural circuitry 202 may be further configured to generate a plurality of blueprint data points. The plurality of blueprint data points may indicate a correspondence between each of the plurality of mental behavioral attributes of the subject 114 and a plurality of signal samples of the set of EEG signals and the set of different types of bio-signals. Each of the generated plurality of blueprint data points may correspond to a different mental behavioral attribute of the set of mental behavioral attributes.

The neural circuitry 202 may be further configured to compare each of the plurality of blueprint data points with other blueprint data points of the plurality of blueprint data points. The mental behavioral attribute of the subject 114 may be identified further based on the comparison. A blueprint data point of a particular mental state of the subject 114 may include information associated with one or more signal patterns (in the set of EEG signals and/or the set of different types of bio-signals), which may correspond to the particular mental behavioral attribute. In the case where the neural circuitry 202 identifies the one or more signal patterns in the plurality of input signals captured from the particular user, the neural circuitry 202 may predict that the particular subject 114 exhibits particular mental behavioral attribute.

Figure 4:
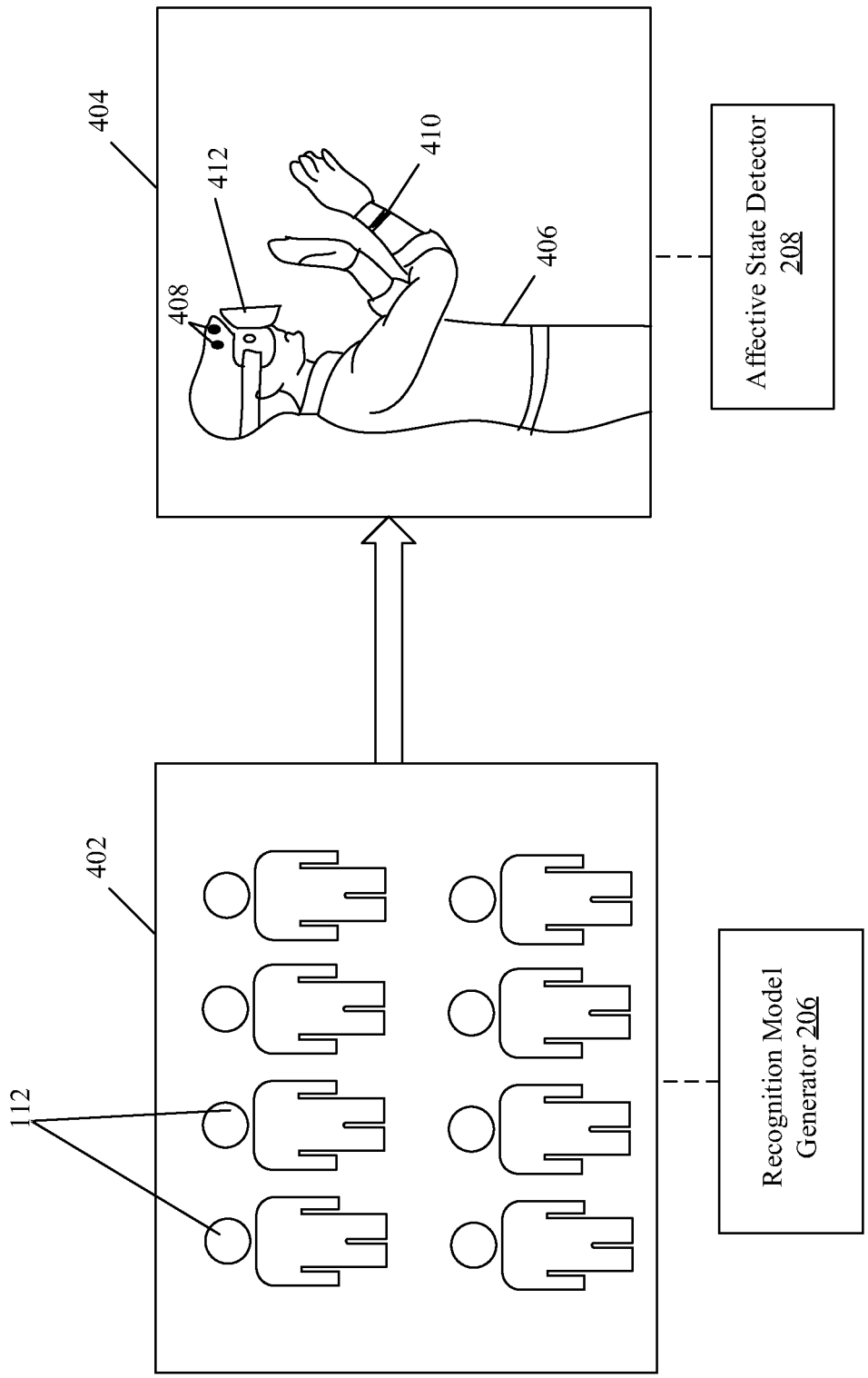
FIG. 4 illustrates a second exemplary scenario for implementation of the electronic device of FIG. 2 for recognition of mental behavioral attributes of a subject based on DNNs, in accordance with an embodiment of the disclosure.

FIG. 4 illustrates a second exemplary scenario for implementation of the electronic device of FIG. 2 for recognition of mental behavioral attributes of a subject based on DNNs, in accordance with an embodiment of the disclosure. FIG. 4 is explained in conjunction with elements from FIGS. 1, 2 and 3. The neural circuitry 202 may be configured to receive a training set of EEG signals and a training set of different types of bio-signals from each training subject of the plurality of training subjects. The training set of EEG signals may include a first training set of EEG signals from a left portion and a second training set of EEG signals from a right portion of a cerebral cortex of the brain of each subject from the set of training subjects.

At 402, the plurality of first recognition models 304 may be trained based on the first training set of EEG signals, the second training set of EEG signals, and the set of different types of bio-signals, as discussed in FIGS. 1 and 3. The recognition model generator 206 may be configured to train the plurality of first recognition models 304 based on the first set of EEG signals, the second set of EEG signals, and the set of different types of bio-signals. The neural circuitry 202 may be configured to estimate a plurality of relationship data between the first set of EEG signals, the second set of EEG signals, and the set of different types of bio-signals, as discussed in FIGS. 1 and 3. The neural circuitry 202 may be configured to train the second recognition model 306 for recognition of the plurality of mental behavioral attributes of the subject, as discussed in FIGS. 1 and 3.

At 404, a set of EEG signals may be captured from a first user 406 within a first time interval, via a set of EEG electrodes 408. A first wearable sensor 410 (which correspond to at least one of the plurality of different types of sensors 110) may be configured to capture at least one type of bio-signal from the first user 406. The affective state detector 208 may be configured to identify or estimate a first mental behavioral attribute of the first user 406, based on the application of the multi-level recognition model 302 on the set of EEG signals and the type of bio-signal. In certain scenarios, the first user 406 may be viewing a media content on a display device (such as a virtual reality (VR) headset 412). In such scenarios, the neural circuitry 202 may be configured to modify the viewed media content based on the identified first mental behavioral attribute of the first user 406.

For example, a set of EEG signals may be captured from a game player (i.e. the first user 406) during a gameplay of a specific VR game on a VR Head Mounted Device (HMD). The HMD device may include an EEG cap that may record the set of EEG signals from a left and a right frontal lobe of the game player over a certain amount of time (say 30 minutes) of gameplay. During the gameplay, the HMD device may load a pre-trained multi-level DNN model in the memory of the HMD device. The pre-trained model may be trained to identify different features, relationships and dependency among different regions of the brain while the game player experiences different mental behavioral attributes, such as excitement, thrill, pain, sad, and happy emotional states. Also, the pre-trained model may be trained to identify if certain features or relationships (indicated by different regions of the brain) can potentially lead to issues (e.g. depression or extreme anger) that may affect the mental health condition of the game player. Thus, the HMD device may have functionalities to alert the game player about a potential health condition or recommend a health professional, and/or a therapeutic medication or regiment to treat the potential condition.

Figure 5A:
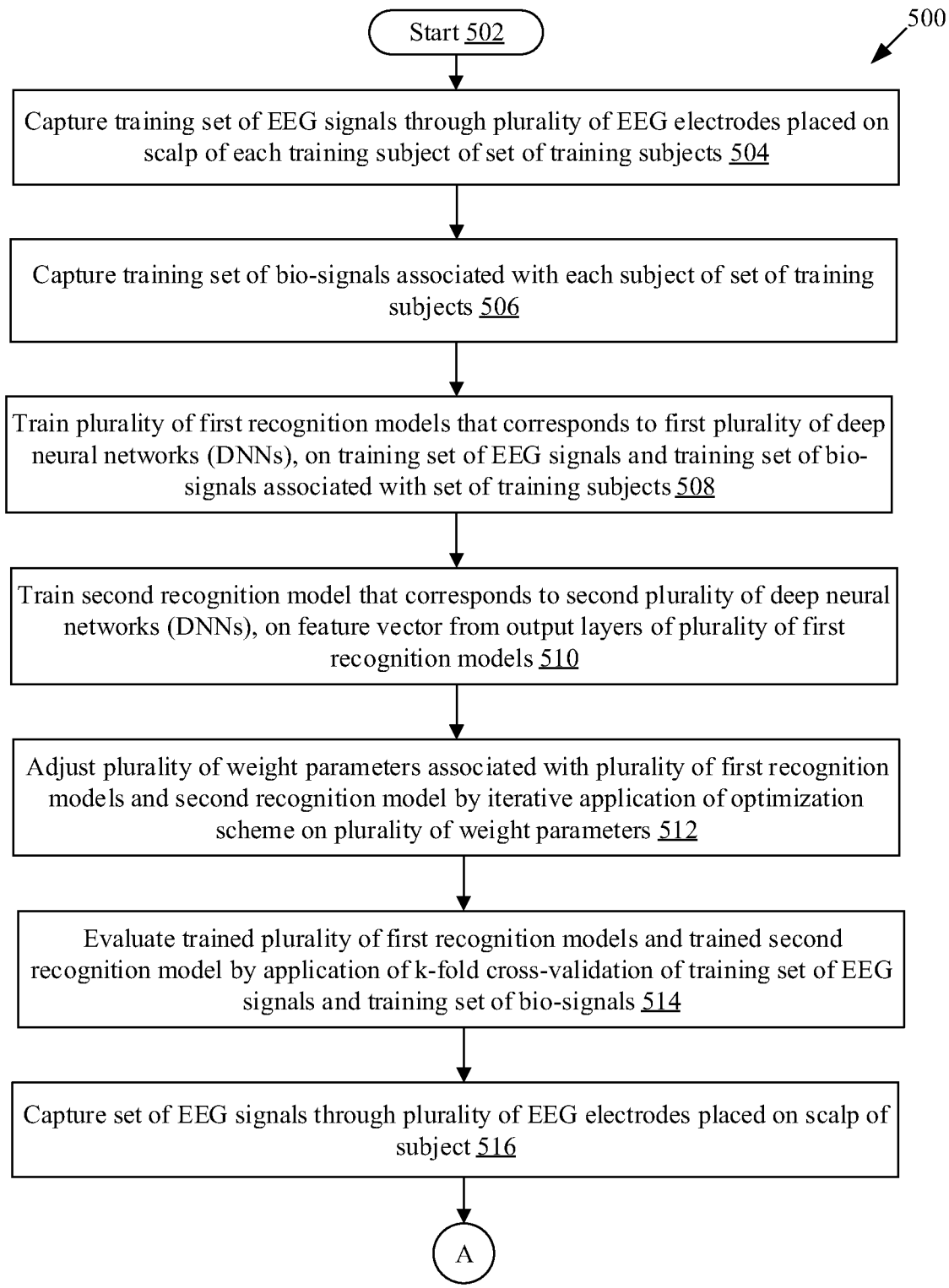
FIGS. 5A, and 5B, collectively, depict a flowchart that illustrates an exemplary method for recognition of mental behavioral attributes of a subject based on DNNs, in accordance with an embodiment of the disclosure.
Figure 5B:
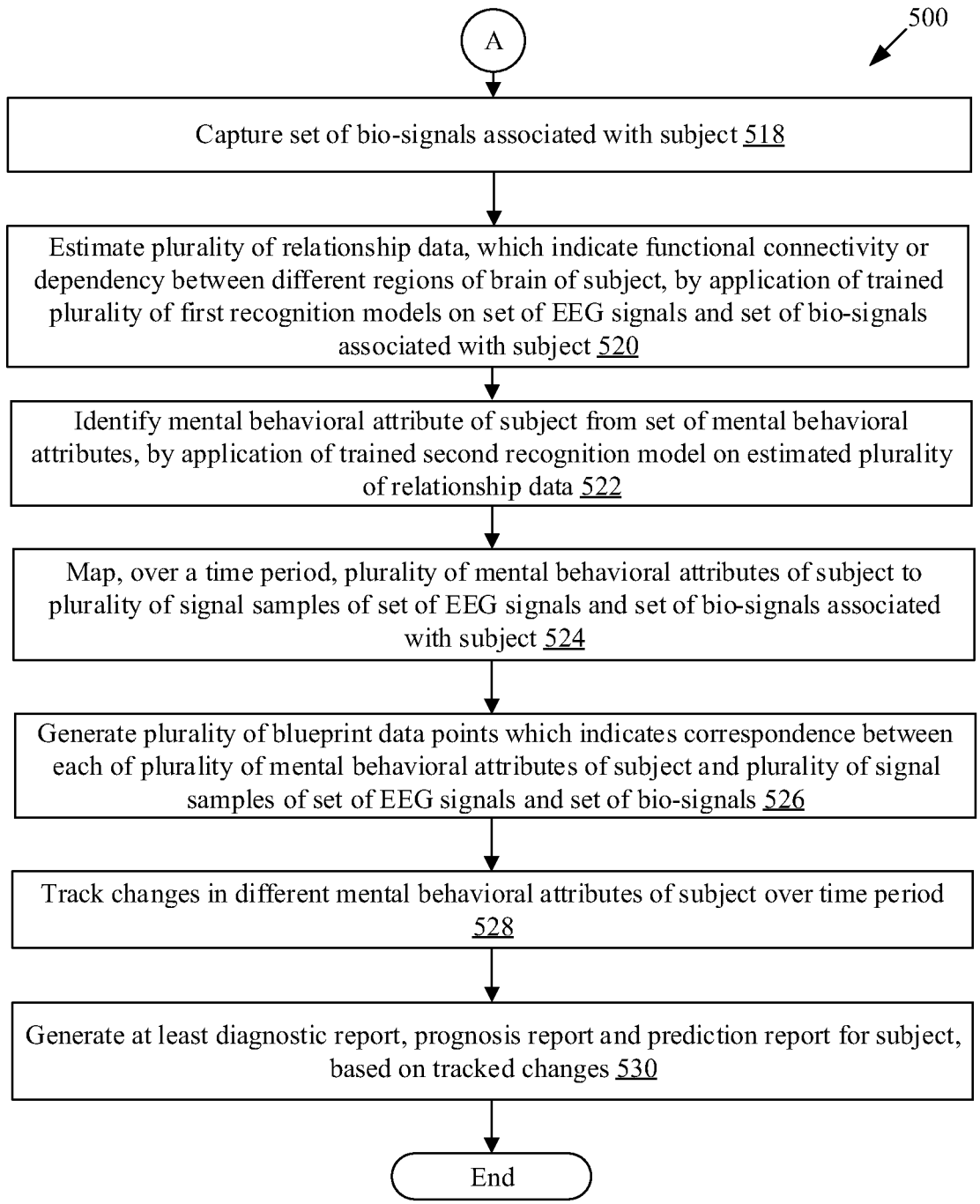

FIGS. 5A, and 5B, collectively, depict a flowchart that illustrates an exemplary method for recognition of mental behavioral attributes of a subject 114 based on DNNs, in accordance with an embodiment of the disclosure. With reference to FIGS. 5A and 5B, there is shown a flowchart 500. The flowchart 500 is described in conjunction with elements from FIGS. 1, 2, 3, and 4. The method starts at 502 and proceeds to 504.

At 504, a training set of EEG signals may be captured through the plurality of EEG electrodes 108, which are placed on a scalp of each training subject of the set of training subjects 112. The neural circuitry 202 may be configured to capture the training set of EEG signals through the plurality of EEG electrodes 108, which are placed on scalp of each training subject of the set of training subjects 112.

At 506, a training set of different types of bio-signals associated with each training subject of the set of training subjects 112 may be captured. The plurality of different types of sensors 110 may be configured to capture the training set of different types of bio-signals associated with each training subject of the set of training subjects 112.

At 508, the plurality of first recognition models 118 that corresponds to a first plurality of DNNs may be trained on a training set of EEG signals and training set of different types of bio-signals associated with the set of training subjects 112. The neural circuitry 202 may be configured to train the plurality of first recognition models 118 that corresponds to a first plurality of DNNs on a training set of EEG signals and a training set of different types of bio-signals associated with the set of training subjects 112.

At 510, the second recognition model 120 that corresponds to a second plurality of DNNs may be trained on a feature vector outputted from output layers of the plurality of first recognition models 118. The neural circuitry 202 may be configured to train the second recognition model 120 that corresponds to a second plurality of DNNs on a feature vector outputted from output layers of the plurality of first recognition models 118.

At 512, a plurality of weight parameters associated with the plurality of first recognition models 118 and the second recognition model 120 may be adjusted by iterative application of an optimization scheme on the plurality of weight parameters. The neural circuitry 202 may be configured to adjust the plurality of weight parameters associated with the plurality of first recognition models 118 and the second recognition model 120 by iterative application of an optimization scheme on the plurality of weight parameters.

At 514, the trained plurality of first recognition models 118 and the trained second recognition model 120 may be evaluated and then optimized by using a randomly selected training, validation and test data subsets, or by application of one or more levels of k-fold cross-validation of the training set of EEG signals and/or the training set of different types of bio-signals. The neural circuitry 202 may be further configured to evaluate the trained plurality of first recognition models 118 and the trained second recognition model 120 by application of k-fold cross-validation of the training set of EEG signals and the training set of bio-signals.

At 516, a set of EEG signals may be captured through the plurality of EEG electrodes 108, which are placed on the scalp of the subject 114. The neural circuitry 202 may be configured to capture a set of EEG signals through the plurality of EEG electrodes 108, which are placed on the scalp of the subject 114.

At 518, a set of different types of bio-signals associated with the subject 114 may be captured. The plurality of different types of sensors 110 may be configured to capture the training set of different types of bio-signals associated with the subject 114.

At 520, a plurality of relationship data, which may indicate a functional connectivity or a dependency between different regions of the brain of the subject 114, may be estimated by application of the trained plurality of first recognition models 118 on the set of EEG signals and the set of different types of bio-signals associated with the subject 114. The neural circuitry 202 may be configured to estimate the plurality of relationship data, which may indicate a functional connectivity or a dependency between different regions of the brain of the subject 114, by application of the trained plurality of first recognition models 118 on the set of EEG signals and the set of different types of bio-signals associated with the subject 114.

At 522, a mental behavioral attribute of the subject 114 may be identified from a set of mental behavioral attributes by application of the trained second recognition model 120 on the estimated plurality of relationship data. The identification of the mental attribute may indicate that a likelihood of presence of the identified mental attribute is maximum from all the remaining attributes in the set of mental behavioral attributes, for a specific portion of EEG signals and bio-signals of the subject 114. The neural circuitry 202 may be configured to identify a mental behavioral attribute of the subject 114 from a set of mental behavioral attributes, by application of the trained second recognition model 120 on the estimated plurality of relationship data.

At 524, a plurality of mental behavioral attributes of the subject 114 may be mapped over a time period to a plurality of signal samples of the set of EEG signals and the set of different types of bio-signals associated with the subject 114. The neural circuitry 202 may be configured to map, over a time period, the plurality of mental behavioral attributes of the subject 114 to a plurality of signal samples of the set of EEG signals and the set of different types of bio-signals associated with the subject 114.

At 526, a plurality of blueprint data, which may indicate a correspondence between each of the plurality of mental behavioral attributes of the subject 114 and the plurality of signal samples of the set of EEG signals and the set of different types of bio-signals may be generated. The neural circuitry 202 may be configured to generate the plurality of blueprint data, which may indicate a correspondence between each of the plurality of mental behavioral attributes of the subject 114 and the plurality of signal samples of the set of EEG signals and the set of different types of bio-signals.

At 528, changes in different mental behavioral attributes of the subject 114 may be tracked over a time period. The neural circuitry 202 may be configured to track changes in different mental behavioral attributes of the subject 114 over a time period.

At 530, at least a diagnostic report, a prognosis report, and a prediction report for the subject 114 may be generated based on the tracked changes. The neural circuitry 202 may be configured to generate at least a diagnostic report, a prognosis report, and a prediction report for the subject 114 may be generated based on the tracked changes. Control passes to end.

Various embodiments of the present disclosure may be found in a method and an electronic device (e.g., the electronic device 102) that handles recognition of mental behavioral attributes based on deep neural networks (DNNs). The electronic device may include a memory (e.g., the memory 210) and neural circuitry (e.g., the neural circuitry 202). The memory may be configured to store a set of electroencephalogram (EEG) signals, a set of different types of bio-signals, and a plurality of user parameters associated with a subject. The neural circuitry may be configured to train a plurality of first recognition models on a training set of EEG signals and a training set of different types of bio-signals associated with a set of training subjects. The plurality of first recognition models may correspond to a first plurality of DNNs. The neural circuitry may be further configured to train a second recognition model that corresponds to a second plurality of deep neural networks DNNs, on a feature vector from output layers of the plurality of first recognition models. Thereafter, the neural circuitry 202 may be configured to estimate a plurality of relationship data, by application of the trained plurality of first recognition models on the set of EEG signals and the set of different types of bio-signals associated with the subject. The plurality of relationship data may indicate a functional connectivity or a dependency between different regions of a brain of the subject. The neural circuitry 202 may be further configured to identify a mental behavioral attribute of the subject from a set of mental behavioral attributes, by application of the trained second recognition model on the estimated plurality of relationship data. In accordance with an embodiment, the identification of the mental behavioral attribute is invariant to an effect of lateralization of affect states, gender, and left-handedness, or right-handedness of the subject on the set of EEG signals and the set of different types of bio-signals.

In accordance with an embodiment, the set of EEG signals may include a first set of EEG signals from a left portion and a second set of EEG signals from a right portion of a cerebral cortex of the brain of the subject. The neural circuitry may be configured to capture, through a plurality of EEG electrodes placed on scalp of the subject, the first set of EEG signals from the left portion and the second set of EEG signals from the right portion of the cerebral cortex of the brain of the subject. The neural circuitry may be further configured to capture, through a plurality of different types of sensors, the set of different types of bio-signals associated with the subject. The plurality of different types of sensors may be placed on different body parts of the subject. The plurality of different types of sensors may include, but are not limited to, a set of neurophysiological sensors, a set of biosensors, and a set of wearable sensors.

In accordance with an embodiment, the training set of EEG signals may include a first training set of EEG signals from a left portion and a second training set of EEG signals from a right portion of a cerebral cortex of the brain of each subject from the set of training subjects. The neural circuitry may be further configured to adjust a plurality of weight parameters associated with the plurality of first recognition models and the second recognition model by an iterative application of optimization scheme on the plurality of weight parameters. The adjustment of the plurality of weight parameters may correspond to a training of the plurality of first recognition models and the second recognition model. In accordance with an embodiment, each recognition model of the plurality of first recognition models may be separately trained on a specific type of signal from the training set of EEG signals and the training set of different types of bio-signals. The neural circuitry may be configured to receive the output feature vector of the trained plurality of first recognition models and an output feature vector of the trained second recognition model. The mental behavioral attribute of the subject may be identified based on the received output feature vector of the trained plurality of first recognition models and the trained second recognition model.

In accordance with an embodiment, the second recognition model may be trained further based on an interconnectivity parameter and a dependency parameter between a first set of mental behavioral attributes of the set of mental behavioral attributes and a second set of mental behavioral attributes of the set of mental behavioral attributes. The set of mental behavioral attributes may include, but are not limited to, a set of affect states, a set of emotional states, a set of mental health conditions, a set of mental states, and a set of mood-based attributes.

In accordance with an embodiment, the neural circuitry may be further configured to map, over a time period, a plurality of mental behavioral attributes of the subject to a plurality of signal samples of the set of EEG signals and the set of different types of bio-signals associated with the subject. The neural circuitry may be further configured to generate a plurality of blueprint data points, which indicates a correspondence between each of the plurality of mental behavioral attributes of the subject and a plurality of signal samples of the set of EEG signals and the set of different types of bio-signals. Each of the generated plurality of blueprint data points may correspond to a different mental behavioral attribute of the set of mental behavioral attributes. The neural circuitry may be further configured to compare each of the plurality of blueprint data points with other blueprint data points of the plurality of blueprint data points. The mental behavioral attribute of the subject may be identified further based on the comparison.

In accordance with an embodiment, an output layer of the second recognition model may act as a classifier to identify the mental behavioral attribute which has a maximum likelihood among the set of mental behavioral attributes. The classifier may be one of a random forest-based classifier, a support vector machine (SVM) based classifier, a logistic regression-based classifier, a linear regression-based classifier, a softmax classifier, a Bayesian estimation network classifier, and a deep neural network classifier.

In accordance with an embodiment, the neural circuitry may be further configured to evaluate and optimize the trained plurality of recognition models and the trained second model. The trained plurality of recognition models and the trained second model may be evaluated by application of a k-fold cross-validation of the training set of EEG signals and the training set of different types of bio-signals.

In accordance with an embodiment, the neural circuitry may be further configured to track changes in different mental behavioral attributes of the subject over a time period. Thereafter, the neural circuitry may be configured to generate at least a diagnostic report, a prognosis report and a prediction report for the subject, based on the tracked changes.

Various embodiments of the present disclosure may be found in a method and an electronic device (e.g., the electronic device 102) that handles recognition of mental behavioral attributes based on deep neural networks (DNNs). The electronic device may include a memory (e.g., the memory 210) and neural circuitry (e.g., the neural circuitry 202). The memory may be configured to store a set of electroencephalogram (EEG) signals, a set of different types of bio-signals, and a plurality of user parameters associated with a subject. The neural circuitry may be configured to input the set of EEG signals and the set of different types of bio-signals associated with the subject to a plurality of first recognition models pre-trained on a training set of EEG signals and a training set of different types of bio-signals. The neural circuitry 202 may be configured to estimate a plurality of relationship data, by application of the trained plurality of first recognition models on the set of EEG signals and the set of different types of bio-signals associated with the subject. The plurality of relationship data may indicate a functional connectivity or a dependency between different regions of a brain of the subject. The neural circuitry 202 may be further configured to identify a mental behavioral attribute of the subject from a set of mental behavioral attributes, by application of the trained second recognition model on the estimated plurality of relationship data. In accordance with an embodiment, the identification of the mental behavioral attribute is invariant to an effect of lateralization of affect states, gender, and left-handedness, or right-handedness of the subject on the set of EEG signals and the set of different types of bio-signals.

Various embodiments of the disclosure may provide a non-transitory computer readable medium and/or storage medium, and/or a non-transitory machine readable medium and/or storage medium having stored thereon, a machine code and/or a set of instructions executable by a machine, such as the electronic device 102, and/or a computer. The set of instructions in the electronic device may cause the machine and/or computer to perform the operations that comprise a storage of a set of electroencephalogram (EEG) signals, a set of different types of bio-signals, and a plurality of user parameters associated with a subject. A plurality of first recognition models may be trained on a training set of EEG signals and a training set of different types of bio-signals associated with a set of training subjects. The plurality of first recognition models may correspond to a first plurality of DNNs. A second recognition model that corresponds to a second plurality of deep neural networks DNNs, may be trained on a feature vector from output layers of the plurality of first recognition models. Thereafter, a plurality of relationship data may be estimated by application of the trained plurality of first recognition models on the set of EEG signals and the set of different types of bio-signals associated with the subject. The plurality of relationship data may indicate a functional connectivity or a dependency between different regions of a brain of the subject. A mental behavioral attribute of the subject may be identified from a set of mental behavioral attributes, by application of the trained second recognition model on the estimated plurality of relationship data. In accordance with an embodiment, the identification of the mental behavioral attribute may be invariant to an effect of lateralization of affect states, gender, and left-handedness, or right-handedness of the subject on the set of EEG signals and the set of bio-signals.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments that fall within the scope of the appended claims.

What is claimed is:

1. An electronic device, comprising:
a memory configured to store a set of electroencephalogram (EEG) signals, a set of different types of bio-signals, and a plurality of user parameters associated with a specific subject; and
at least one processor configured to:
train a plurality of first recognition models, that includes a first plurality of deep neural networks (DNNs), on a training set of EEG signals and a training set of different types of bio-signals associated with a set of training subjects, wherein
a first DNN of the plurality of DNNs is trained based on a first training set of EEG signals of the training set of EEG signals,
each EEG signal of the first training set of EEG signals corresponds to a first region of a brain of a respective training subject of the plurality of training subjects,
a second DNN of the plurality of DNNs is trained based on a second training set of EEG signals of the training set of EEG signals,
each EEG signal of the second training set of EEG signals corresponds to a second region of the brain of the respective training subject of the plurality of training subjects,
the first region is different from the second region, and
the set of training subjects is different from the specific subject;
train a second recognition model, that corresponds to a second plurality of deep neural networks (DNNs), on a feature vector from output layers of the plurality of first recognition models, wherein
the second recognition model is trained based on an interconnectivity parameter and a dependency parameter between a first set of mental behavioral attributes of a set of mental behavioral attributes and a second set of mental behavioral attributes of the set of mental behavioral attributes,
the interconnectivity parameter indicates a functional connectivity between a first region of a brain of the specific subject and a second region of the brain of the specific subject in a case in which the brain of the specific subject stays functional for at least two mental behavioral attributes of the set of mental behavioral attributes,
the first region of the brain of the specific subject is different from the second region of the brain of the specific subject,
the first region of the brain of the specific subject corresponds to an emotional state of the specific subject,
the second region of the brain of the specific subject corresponds to a body movement of the specific subject, and
the dependency parameter indicates an effect of a first mental behavioral attribute of the set of mental behavioral attributes on a second mental behavioral attribute of the set of mental behavioral attributes;
estimate a plurality of relationship data, which indicates one of the functional connectivity or a dependency between the first region of the brain of the specific subject and the second region of the brain of the specific subject,
wherein the plurality of relationship data is estimated by application of the trained plurality of first recognition models on the set of EEG signals associated with the specific subject and the set of different types of bio-signals associated with the specific subject; and
identify a specific mental behavioral attribute of the specific subject from the set of mental behavioral attributes, by application of an output layer of the trained second recognition model on the estimated plurality of relationship data.

2. The electronic device according to claim 1, wherein the set of EEG signals associated with the specific subject comprises a first set of EEG signals from a left portion of the brain of the specific subject and a second set of EEG signals from a right portion of a cerebral cortex of the brain of the specific subject.

3. The electronic device according to claim 2, wherein the at least one processor is further configured to capture, via a plurality of EEG electrodes placed on scalp of the specific subject, the first set of EEG signals from the left portion of the cerebral cortex of the brain of the specific subject and the second set of EEG signals from the right portion of the cerebral cortex of the brain of the specific subject.

4. The electronic device according to claim 1, wherein the at least one processor is further configured to capture, via a plurality of different types of sensors, the set of different types of bio-signals associated with the specific subject.

5. The electronic device according to claim 4, wherein the plurality of different types of sensors is placed on different body parts of the specific subject.

6. The electronic device according to claim 5, wherein the plurality of different types of sensors comprises at least one of a set of neurophysiological sensors, a set of biosensors, or a set of wearable sensors.

7. The electronic device according to claim 1, wherein
the first region of the brain of the respective training subject corresponds to a left portion of a cerebral cortex of the brain of the respective training subject, and
the second region of the brain of the respective training subject corresponds to a right portion of the cerebral cortex of the brain of the respective training subject.

8. The electronic device according to claim 1, wherein
the at least one processor is further configured to adjust a plurality of weight parameters associated with the plurality of first recognition models and the second recognition model based on an iterative application of an optimization scheme on the plurality of weight parameters, and
the plurality of weight parameters is adjusted to train the plurality of first recognition models and the second recognition model.

9. The electronic device according to claim 1, wherein
the at least one processor is further configured to receive the feature vector of the trained plurality of first recognition models and an output feature vector of the trained second recognition model, and
the specific mental behavioral attribute of the specific subject is identified based on the received feature vector of the trained plurality of first recognition models and the output feature vector of the trained second recognition model.

10. The electronic device according to claim 1, wherein the set of mental behavioral attributes comprises at least one of a set of affect states, a set of emotional states, a set of mental health conditions, a set of mental states or conditions, a set of psychological states or conditions, or a set of mood-based attributes.

11. The electronic device according to claim 1, wherein the identification of the specific mental behavioral attribute is invariant to one of an effect of lateralization of affect states, gender, and left-handedness, or right-handedness of the specific subject on the set of EEG signals associated with the specific subject and the set of different types of bio-signals associated with the specific subject.

12. The electronic device according to claim 1, wherein the at least one processor is further configured to map, over a time period, a plurality of mental behavioral attributes of the specific subject to a plurality of signal samples of the set of EEG signals associated with the specific subject and the set of different types of bio-signals associated with the specific subject.

13. The electronic device according to claim 12, wherein the at least one processor is further configured to generate a plurality of blueprint data points, which indicates a correspondence between each of the plurality of mental behavioral attributes of the specific subject and the plurality of signal samples of the set of EEG signals associated with the specific subject and the set of different types of bio-signals associated with the specific subject.

14. The electronic device according to claim 13, wherein
each of the generated plurality of blueprint data points corresponds to a different mental behavioral attribute of the set of mental behavioral attributes, and
the at least one processor is further configured to:
compare each of the plurality of blueprint data points with other blueprint data points of the plurality of blueprint data points; and
identify the specific mental behavioral attribute of the specific subject based on the comparison.

15. The electronic device according to claim 1, wherein
the output layer of the trained second recognition model acts as a classifier to identify the specific mental behavioral attribute which has a maximum likelihood among the set of mental behavioral attributes, and
the classifier is at least one of a random forest-based classifier, a support vector machine (SVM)-based classifier, a logistic regression-based classifier, a linear regression-based classifier, a softmax classifier, a Bayesian estimation network classifier, or a deep neural network classifier.

16. The electronic device according to claim 1, wherein the at least one processor is further configured to
evaluate and optimize the trained plurality of first recognition models and the trained second recognition model based on a randomly selected training, validation and test data subsets, or by application of at least one level of k-fold cross-validation of the training set of EEG signals and the training set of different types of bio-signals.

17. The electronic device according to claim 1, wherein the at least one processor is further configured to:
track changes in different mental behavioral attributes of the specific subject over a time period; and
generate a diagnostic report, a prognosis report, and a prediction report for the specific subject based on the tracked changes.

18. The electronic device according to claim 1, wherein the first set of mental behavioral attributes is different from the second set of mental behavioral attributes.

19. An electronic device, comprising:
a memory configured to store a set of electroencephalogram (EEG) signals, a set of bio-signals, and a plurality of user parameters associated with a specific subject; and
at least one processor configured to:
input the set of EEG signals and the set of bio-signals associated with the specific subject to a plurality of first recognition models pre-trained on a training set of EEG signals and a training set of different types of bio-signals associated with a set of training subjects, wherein
the plurality of first recognition models includes a first plurality of deep neural networks (DNNs),
a first DNN of the plurality of DNNs is pre-trained based on a first training set of EEG signals of the training set of EEG signals,
each EEG signal of the first training set of EEG signals corresponds to a first region of a brain of a respective training subject of the plurality of training subjects,
a second DNN of the plurality of DNNs is pre-trained based on a second training set of EEG signals of the training set of EEG signals, each EEG signal of the second training set of EEG signals corresponds to a second region of the brain of the respective training subject of the plurality of training subjects, the first region is different from the second region, and the set of training subjects is different from the specific subject;

estimate a plurality of relationship data, which indicates one of a functional connectivity or a dependency between a first region of a brain of the specific subject and a second region of the brain of the specific subject, wherein the plurality of relationship data is estimated by application of the pre-trained plurality of first recognition models on the set of EEG signals associated with the specific subject and the set of bio-signals associated with the specific subject; and identify a specific mental behavioral attribute of the specific subject from a set of mental behavioral attributes, by application of an output layer of a second recognition model on the estimated plurality of relationship data, wherein the second recognition model is pre-trained on a feature vector from output layers of the plurality of first recognition models, the second recognition model is pre-trained based on an interconnectivity parameter and a dependency parameter between a first set of mental behavioral attributes of the set of mental behavioral attributes and a second set of mental behavioral attributes of the set of mental behavioral attributes, the interconnectivity parameter indicates the functional connectivity between the first region of the brain of the specific subject and the second region of the brain of the specific subject in a case in which the brain of the specific subject stays functional for at least two mental behavioral attributes of the set of mental behavioral attributes, the first region of the brain of the specific subject is different from the second region of the brain of the specific subject, the first region of the brain of the specific subject corresponds to an emotional state of the specific subject, the second region of the brain of the specific subject corresponds to a body movement of the specific subject, and the dependency parameter indicates an effect of a first mental behavioral attribute of the set of mental behavioral attributes on a second mental behavioral attribute of the set of mental behavioral attributes.

20. A method, comprising:

in an electronic device that comprises a memory and at least one processor:

storing, by the memory, a set of electroencephalogram (EEG) signals, a set of bio-signals, and a plurality of user parameters associated with a specific subject;

training, by the at least one processor, a plurality of first recognition models, that includes a first plurality of deep neural networks (DNNs), on a training set of EEG signals and a training set of bio-signals associated with a set of training subjects, wherein a first DNN of the plurality of DNNs is trained based on a first training set of EEG signals of the training set of EEG signals, each EEG signal of the first training set of EEG signals corresponds to a first region of a brain of a respective training subject of the plurality of training subjects, a second DNN of the plurality of DNNs is trained based on a second training set of EEG signals of the training set of EEG signals, each EEG signal of the second training set of EEG signals corresponds to a second region of the brain of the respective training subject of the plurality of training subjects, the first region is different from the second region, and the set of training subjects is different from the specific subject;

training, by the at least one processor, a second recognition model that corresponds to a second plurality of deep neural networks (DNNs), on a feature vector from output layers of the plurality of first recognition models, wherein the second recognition model is trained based on an interconnectivity parameter and a dependency parameter between a first set of mental behavioral attributes of a set of mental behavioral attributes and a second set of mental behavioral attributes of the set of mental behavioral attributes, the interconnectivity parameter indicates a functional connectivity between a first region of a brain of the specific subject and a second region of the brain of the specific subject in a case in which the brain of the specific subject stays functional for at least two mental behavioral attributes of the set of mental behavioral attributes, the first region of the brain of the specific subject is different from the second region of the brain of the specific subject, the first region of the brain of the specific subject corresponds to an emotional state of the specific subject, the second region of the brain of the specific subject corresponds to a body movement of the specific subject, and the dependency parameter indicates an effect of a first mental behavioral attribute of the set of mental behavioral attributes on a second mental behavioral attribute of the set of mental behavioral attributes;

estimating, by the at least one processor, a plurality of relationship data, which indicates one of the functional connectivity or a dependency between the first region of the brain of the specific subject and the second region of the brain of the specific subject, wherein the plurality of relationship data is estimated by application of the trained plurality of first recognition models on the set of EEG signals associated with the specific subject and the set of bio-signals associated with the specific subject; and identifying, by the at least one processor, a specific mental behavioral attribute of the specific subject from the set of mental behavioral attributes, by application of an output layer of the trained second recognition model on the estimated plurality of relationship data.

* * * * *